(12) United States Patent
Jiang et al.

(10) Patent No.: US 10,935,491 B2
(45) Date of Patent: Mar. 2, 2021

(54) MEMRISTOR-RECONSTRUCTED NEAR-INFRARED SPR BIOSENSOR WITH ADJUSTABLE PENETRATION DEPTH AND PREPARATION METHOD THEREOF

(71) Applicant: University of Electronic Science and Technology of China, Sichuan (CN)

(72) Inventors: Xiangdong Jiang, Sichuan (CN); Ruikang Guo, Sichuan (CN); Xiang Dong, Sichuan (CN); Jimin Wang, Sichuan (CN); Wei Li, Sichuan (CN)

(73) Assignee: University of Electronic Science and Technology of China, Sichuan (CN)

( * ) Notice: Subject to any disclaimer, the term of this patent is extended or adjusted under 35 U.S.C. 154(b) by 22 days.

(21) Appl. No.: 16/502,624

(22) Filed: Jul. 3, 2019

(65) Prior Publication Data

US 2019/0323963 A1 Oct. 24, 2019

(30) Foreign Application Priority Data

Apr. 24, 2019 (CN) .......................... 201910333435.0

(51) Int. Cl.
*G01N 21/552* (2014.01)
*G01N 21/65* (2006.01)
(Continued)

(52) U.S. Cl.
CPC ........... *G01N 21/553* (2013.01); *G01N 21/35* (2013.01); *G01N 21/658* (2013.01);
(Continued)

(58) Field of Classification Search
CPC .... G01N 21/553; G01N 21/35; G01N 21/658; G01N 21/7703; G01N 33/48; G01N 2021/258; G02B 6/102
See application file for complete search history.

(56) References Cited

U.S. PATENT DOCUMENTS 5,898,503 A * 4/1999 Keller .................. G01N 21/553
356/445
5,912,456 A * 6/1999 Melendez ............ G01N 21/553
250/216
(Continued)

FOREIGN PATENT DOCUMENTS

CN 106289329 A * 1/2017

OTHER PUBLICATIONS

Jihang Lee et al., On-Demand Reconfiguration of Nanomaterials: When Electronics Meets Lonics, Advanced Materials 2018, 30, 1702770.
(Continued)

*Primary Examiner* — Blake C Riddick

(57) ABSTRACT

A memristor-reconstructed near-infrared SPR biosensor with adjustable penetration depth includes a prism, a first non-conductive dielectric film layer, a metal film layer, a second non-conductive dielectric film layer and a conductive dielectric film layer, wherein the prism is configured to generate an ATR (Attenuated Total Reflections) attenuation evanescent wave; the first non-conductive dielectric film layer, the metal film layer, and the second non-conductive dielectric film layer define a sensing unit for achieving a basic sensing function; the metal film layer, the second non-conductive dielectric film layer and the conductive dielectric film layer define a memristive unit; a voltage applying device is provided between the first electrode and the second electrode for applying a bias voltage to the memristive unit so as to realize infrared memristive reconfiguration. A preparation method and a penetration depth tuning method of the memristor-reconstructed near-infrared SPR biosensor with adjustable penetration depth are also disclosed.

13 Claims, 6 Drawing Sheets

(51) Int. Cl.
*G02B 6/10* (2006.01)
*G01N 21/35* (2014.01)
*G01N 33/48* (2006.01)
*G01N 21/77* (2006.01)
*G01N 21/25* (2006.01)

(52) U.S. Cl.
CPC ......... *G01N 21/7703* (2013.01); *G01N 33/48* (2013.01); *G02B 6/102* (2013.01); *G01N 2021/258* (2013.01)

(56) References Cited

U.S. PATENT DOCUMENTS

| | | | | |
|---|---|---|---|---|
| 5,946,083 | A * | 8/1999 | Melendez | G01N 21/553 356/317 |
| 6,045,756 | A * | 4/2000 | Carr | G01N 21/7703 422/534 |
| 6,798,521 | B2 * | 9/2004 | Elkind | G01N 21/553 356/445 |
| 7,407,817 | B2 * | 8/2008 | Ho | G01N 21/553 349/56 |
| 2006/0183982 | A1 * | 8/2006 | Shioi | A61B 5/14532 600/310 |
| 2011/0128546 | A1 * | 6/2011 | Couillard | G01N 21/553 356/445 |
| 2017/0016813 | A1 * | 1/2017 | Wagner | G01N 21/53 |
| 2018/0113330 | A1 * | 4/2018 | Maguire-Boyle | G02F 1/091 |

OTHER PUBLICATIONS

Sivan Isaacs et al., Long range surface plasmon resonance with ultra-high penetration depth for self-referenced sensing and ultra-low detection limit using diverging beam approach, Applied Physics Letters 106, 193701 (2015).

* cited by examiner

MEMRISTOR-RECONSTRUCTED NEAR-INFRARED SPR BIOSENSOR WITH ADJUSTABLE PENETRATION DEPTH AND PREPARATION METHOD THEREOF

CROSS REFERENCE OF RELATED APPLICATION

The present invention claims priority under 35 U.S.C. 119(a-d) to CN 201910333435.0, filed Apr. 24, 2019.

BACKGROUND OF THE PRESENT INVENTION

Field of Invention

The present invention relates to the field of surface plasmon resonance biosensor, and more particularly to a biosensor with tunable penetration depth, and more particularly to a memristor-reconstructed near-infrared SPR biosensor with adjustable penetration depth and a preparation method thereof.

Description of Related Arts

Surface plasmon resonance (SPR) is an optical phenomenon discovered by Wood in the early 20th century. Plasma resonance was produced in the early days by electron beam bombarding metal surface in vacuum. In the 1960s, two scientists from West Germany, Otto and Kretchmann, invented a method of exciting surface ions by visible light. Until the 1980s, scientist Liedberg from Sweden used this technique to detect interactions between biomolecules.

Surface plasmon polaritons (SPPs) the key to the generation of SPR, which is free charge oscillation generated under a specific light wave field on an interface between a dielectric medium and a metal medium. Light is able to cause excitation of SPPs. When the wave vector of the incident light matches the wave vector of the surface plasma, surface plasmon resonance (SPR) occurs. Because this wave matching condition is easily affected by change of the small dielectric constant on the interface, it is able to be used to accurately detect changes in the refractive index of the adsorption layer (cells, bacteria, etc.) on the metal surface. Therefore, various SPR biosensors based on the attenuated total reflection (ATR) method have emerged. The research finds that SPR technology has the advantages of high sensitivity, high selectivity, real-time detection, mark-free, small size and low cost. Therefore, it is widely used in the field of detection and has a promising future.

Penetration depth is an important indicator of SPR biosensors and is defined as the traveled distance when the evanescent wave energy on the Z-axis decays to 1/e of the maximum value. Traditional SPR sensors are only able to produce low penetration depth due to metal absorption. Although small penetration depths help to make the SPR sensor more specific by attaching the receptor layer to the surface, when the size of the analyte (such as cell) is equal to or larger than the penetration depth that the sensor is able to reach, traditional SPR sensors are limited.

One way to overcome the low penetration depth is to use infrared light sensing. The infrared light itself has the advantage of long propagation distance, short-wave infrared (with a wavelength within 1.5 μm) for biosensing and near-infrared for red light are able to penetrate into the deepest device, the penetration depth is able to reach 10 mm, which is able to directly affect the skin's blood vessels, lymphatic vessels, nerve endings and other subcutaneous tissue.

Another method is to adopt different SPR biosensor structures to generate different penetration depths. In the biosensor classification using electromagnetic (EM) field to enhance the surface SPR excitation of metal film, four basic types are identified, namely, traditional SPR, long-range SPR (LRSPR, Long-Range Surface Plasmon Resonance), coupled plasma waveguide resonance (CPWR), and waveguide coupled SPR (WCPR).

(1) The traditional SPR surface plasma wave is exponentially decayed along the normal direction of the interface, and the effective penetration depth is only about 300 nm. Although this characteristic is very sensitive to the change of the refractive index near the interface, it is unable to effectively detect macromolecules such as viruses, bacteria and proteins. Traditional surface plasma resonance technology indicators reach bottlenecks and are difficult to be improved.

(2) The LRSPR biosensor introduces a dielectric buffer layer between the prism and the metal layer of the conventional SPR biosensor. When the refractive index of the dielectric buffer layer is equal to that of the object to be tested, a symmetrical environment is achieved, so that the propagation length of the SPW (surface plasma wave oscillated and propagated by SPPs) exceeds the propagation length of the conventional SPW, and the energy of the incident beam is preserved. The advantage is that the LRSPR device has a very sharp reflectivity (namely, large depth-to-width ratio), and the penetration depth of the special LRSPR biosensor is able to reach above 3 μm. The disadvantage is that the LRSPR depends on the existence of the symmetric environment.

(3) The CPWR biosensor combines the waveguide layer beneath the surface of a conventional SPR biosensor. The interference of the waveguide layer in the CPWR device causes steep angles in both the longitudinal (TM) and transverse (TE) modes, with the advantage of having a good depth-width which reaches 2 μm. The disadvantage is that the biosensing surface is quite far from the SPW at the interface between the metal film layer and the waveguide layer, and its sensitivity is still about 10 times lower than that of the conventional SPR device.

(4) WCSPR comprises two metal layers and one waveguide layer. The WCSPR combines SPR with the waveguide mode, which not only preserves the sensitivity of the biosensor, but also produces a steeper degradation of reflectance spectrum, thereby improving the measurement accuracy. The disadvantage is that the matching conditions are harsh.

The membrane structures of the above four SPR biosensors are fixed, and thus their penetration depth is immutable. However, these biosensors have a fixed penetration depth in a range of about 200 to about 300 nm and are incapable of detecting different layers or depths, i.e., chemical and biological events with different penetration depths. However, for different analytes such as proteins, bacteria, dispersed cells, and living cells with different sizes, especially for larger unknown biochemical materials, the AIR (Attenuated Total Reflection) decay evanescent wave generated by the sensor with a fixed penetration depth is only able to partially sense the organism and is unable to get all the information. On the contrary, when a sensor with large penetration depth is used to sense a small-sized organism, the resonance-enhanced surface plasma wave will penetrate through the organism to the outside environment, causing large external interference, and the resolution will be reduced.

The memristor is a non-linear resistor with memory function. It is able to be used not only for storing data, but also for logic calculation. It has a memristive effect, and the inside of the memristor is generally a metal-medium-metal (or conductive medium) sandwich structure. The principle is to use voltage to drive electrochemical metallization (ECM) of metal ions, and form metal nanofilaments in the dielectric layer. The filaments have a modulation effect on light propagation, and microscopically change the dielectric constant of the original medium.

SUMMARY OF THE PRESENT INVENTION

A technical problem to be solved by the present invention is to provide a memristor-reconstructed near-infrared SPR biosensor with adjustable penetration depth and a preparation method thereof, which adopts memristor-reconstructed electrochemical metallization mechanism to achieve the tunable penetration depth of the biosensor.

To solve the above technical problem, the present invention provides technical solutions as follows.

A memristor-reconstructed near-infrared SPR biosensor with adjustable penetration depth, which comprises:

a prism, and a first non-conductive dielectric film layer, a metal film layer, a second non-conductive dielectric film layer and a conductive dielectric film layer all of which are located at a bottom of the prism in sequence, wherein:

the prism is configured to generate an ATR (Attenuated Total Reflection) attenuation evanescent wave under incident excitation of infrared light;

the first non-conductive dielectric film layer, the metal film layer, and the second non-conductive dielectric film layer define a sensing unit, the first non-conductive dielectric film layer and the second non-conductive dielectric film layer form a symmetric environment, the sensing unit is configured to implement an LRSPR (Long Range Surface Plasmon Resonance) effect so as to realize a basic sensing function of the SPR (Surface Plasmon Resonance) sensor;

the metal film layer, the second non-conductive dielectric film layer and the conductive dielectric film layer define a memristive unit, wherein: the metal film layer acts as a first electrode, the conductive dielectric film layer acts as a second electrode, the first electrode is perpendicular to the second electrode for forming a CROSSBAR structure, the first electrode is electrically connected with the second electrode, a voltage applying device is provided between the first electrode and the second electrode for applying a positive or negative bias voltage to the memristive unit so as to realize infrared memristive reconfiguration.

Preferably, the prism is a Si prism (whose refractive index is able to reach 3.5) or a Ge prism with a larger refractive index which is able to satisfy conditions of total reflection of light waves.

Preferably, a wavelength the infrared light is 1310 nm or 1550 nm; the infrared light is able to balance the low dispersion of the communication wavelength with its own long propagation distance.

Preferably, the first non-conductive dielectric film layer is made from a-Si (amorphous silicon) and has a thickness in a range of 180 to 220 nm.

Preferably, the metal film layer is made of Ag and has a thickness in a range of 35 to 42 nm.

Preferably, the second non-conductive dielectric film layer is made from a-Si and has a thickness in a range of 230 to 300 nm.

Since a symmetrical environment needs to be formed, the first non-conductive dielectric film and the second non-conductive dielectric film are made from a same material, and other non-conductive dielectric films such as $SiO_2$ is also able to be used.

Preferably, the conductive dielectric film layer is made from IMO (indium tin oxide doped with molybdenum), and has a thickness in a range of 40 to 60 nm, and more preferably, a refractive index of the conductive dielectric film layer is 1.84.

Preferably, the metal film layer is perpendicular to the conductive dielectric film layer to define the CROSSBAR structure so as to ensure that an ohmic contact resistance is small enough.

Preferably, both of the first electrode and the second electrode have a comb-shaped structure which comprises multiple comb teeth, a line width of every comb tooth is 20 nm, a spacing of every two adjacent comb teeth is 20 nm, a width of each of the first electrode and the second electrode is in a range of 0.2 to 1 µm, and a size of each of the first electrode and second electrode is 1×0.5×0.5 µm.

A method for manufacturing the memristor-reconstructed near-infrared. SPR biosensor with adjustable penetration depth, which comprises steps of:

(S1) depositing a first non-conductive dielectric film layer on a bottom of a prism through RF (radio frequency) magnetron sputtering;

(S2) depositing a metal film layer on the first non-conductive dielectric film layer through DC (direct current) magnetron sputtering, performing coating and photoetching on the metal film layer, obtaining multiple first grooves with an equal line width and an equal spacing to form a first electrode of a memristive unit for generating SPR (Surface Plasmon Resonance) in a sensing unit through light excitation, wherein the equal line width is as same as the equal spacing;

(S3) depositing a second non-conductive dielectric film layer on the metal film layer through RE magnetron sputtering;

(S4) depositing a conductive dielectric film layer on the second non-conductive dielectric film layer through RF magnetron sputtering, performing coating and photoetching on the conductive dielectric film layer, obtaining multiple second grooves with the equal line width and the equal spacing to form a second electrode of the memristive unit which combines with the first electrode to form a CROSSBAR structure; and (S5) electrically connecting the first electrode with the second electrode, providing a voltage applying device between the first electrode and the second electrode for applying a bias voltage to the memristive unit.

Preferably, in the step of (S1), the prism is a Si prism (whose refractive index is able to reach 3.5) or a Ge prism with a larger refractive index which is able to satisfy conditions of total reflection of light waves.

Preferably, in the step of (S1), the first non-conductive dielectric film layer is made from a-Si (amorphous silicon) and has a thickness in a range of 180 to 220 nm, and more preferably 200 nm.

Preferably, in the step of (S2), the metal film layer is made of Ag and has a thickness in a range of 35 to 42 nm, and more preferably 35 nm.

Preferably, the second non-conductive dielectric film layer is made from a-Si (amorphous silicon) and has a thickness in a range of 230 to 300 nm, and more preferably 300 nm.

Since a symmetrical environment needs to be formed, the first non-conductive dielectric film and the second non-conductive dielectric film are made from a same material, and other non-conductive dielectric films such as $SiO_2$ is also able to be used.

Preferably, in the step of (S4), the conductive dielectric film layer is made from IMO (indium tin oxide doped with molybdenum), and has a thickness in a range of 40 to 60 nm, and more preferably 50 nm, a refractive index of the conductive dielectric film layer is 1.84.

Preferably, both of the first electrode and the second electrode have a comb-shaped structure which comprises multiple comb teeth, a line width of every comb tooth is 20 nm, a spacing of every two adjacent comb teeth is 20 nm, a width of each of the first electrode and the second electrode is in a range of 0.2 to 1 μm, and a size of each of the first electrode and second electrode is 1×0.5×0.5 μm.

The present invention also provides a method for tuning a penetration depth of the memristor-reconstructed near-infrared SPR biosensor with adjustable penetration depth, which comprises steps of:

applying a positive bias voltage to the memristive unit by a voltage applying device, electrochemically metallizing the metal film layer, a metal material of the metal film layer growing metal nanofilaments in the second non-conductive dielectric film layer through oxidation-reduction, changing a dielectric constant of a partial area of the original second non-conductive dielectric film layer, destroying a symmetrical environment of the first non-conductive dielectric film layer and the second non-conductive dielectric film layer of the sensing unit, and reducing the penetration depth of the sensor; or applying a negative bias voltage to the memristive unit by the voltage applying device, migrating the metal nanofilaments in the second non-conductive dielectric film layer back to the metal film layer, restoring the symmetrical environment of the first non-conductive dielectric film layer and the second non-conductive dielectric film layer of the sensing unit, and reducing the penetration depth of the sensor; and restoring the penetration depth of the sensor back to a penetration depth without applying the negative bias voltage to the memristive unit.

A working principle of the biosensor according to the preferred embodiment of the present invention is as follows.

(1) Implementation of Basic Sensing Function of SPR Biosensor

When there is no bias voltage is applied to the memrist unit, the biosensor comprises the prism, the first non-conductive dielectric film layer, the metal film layer, the second non-conductive dielectric film layer, the conductive dielectric film layer and the biological organism to be tested in sequence. The SPR biosensor adopts an angle mode to align infrared light with a center of the CROSSBAR structure. Through the normalized reflection spectrum method, when the refractive index of the biological organism to be tested changes, the resonance angle correspondingly changes, so as to achieve the basic sensing function of the SPR biosensor.

When a positive bias voltage is applied to the memrist unit which has a sandwich structure defined by the metal film layer, the second non-conductive dielectric film layer and the conductive dielectric film layer, the metal film layer is electrochemically metallized, metal nanofilaments grow in the second non-conductive dielectric film layer through oxidation-reduction, and at this time, the biosensor comprises the prism, the first non-conductive dielectric film layer, the metal film layer, the second non-conductive dielectric film layer: the metal film layer, the conductive dielectric film layer and the biological organism to be tested in sequence. At this time, the SPR biosensor still adopts the angle mode to align infrared light with the center of the CROSSBAR structure. Through the normalized reflection spectrum method, when the refractive index of the biological organism to be tested changes, the resonance angle correspondingly changes, so as to achieve the basic sensing function of the SPR biosensor.

Similarly, when a negative bias voltage is applied to the memrist unit, the metal nanofilaments grown in the second non-conductive dielectric film layer migrate back to the metal film layer under the action of the reverse electric field, so as to achieve the basic sensing function of the SPR biosensor.

(2) Implementation of Penetration Depth Tuning Function of SPR Biosensor

When there is no bias voltage is applied to the meimist unit, the SPR biosensor adopts the angle mode to align infrared light with the center of the CROSSBAR channel. When the prism is excited by infrared light, and a sandwich structure of the sensing unit defined by the first non-conductive dielectric film layer, the metal film layer and the second non-conductive dielectric film layer forms the LRSRP effect, and at this time, the LRSRP has an ultra-long penetration depth due to its very high symmetrical environment.

When a positive bias voltage is applied to the memrist unit, the SPR biosensor still adopts the angle mode, the memrist unit has the sandwich structure defined by the metal film layer, the second non-conductive dielectric film layer and the conductive dielectric, the metal film layer of the sandwich structure is electrochemically metallized, a material material of the metal film layer grows metal nanofilaments in the second non-conductive dielectric film layer by redox reaction, and at this time, the biosensor comprises the prism, the first non-conductive dielectric film layer, the metal film layer, the second non-conductive dielectric film layer containing metal nanofilaments, the conductive dielectric film layer and the biological organism to be tested in sequence. Due to the reconstitution mechanism of the memristive effect, compared with the original second non-conductive dielectric film layer, the second non-conductive dielectric film layer containing the metal nanofilaments changes in a dielectric constant, which destroys the symmetrical environment of the refractive index of the original device, that is, destroys the formation conditions of LRSPR, so that the penetration depth of the original LRSPR with the ultra-long penetration depth is gradually reduced, Within a certain range, the penetration depth gradually decreases with the bias voltage increases.

When a negative bias voltage is applied to the memrist unit, and infrared light is aligned with the center of the CROSSBAR channel, the metal nanofilaments grown in the second non-conductive dielectric film layer migrate back to the metal film layer under the action of the reverse electric field; under the excitation of infrared light, the whole biosensor structure gradually changes back to the case of no voltage bias. At this time, the LRSPR effect is formed and the ultra-long penetration depth is formed. That is, within a certain range, with the reverse bias voltage increases, the penetration depth gradually increases.

The present invention utilizes the memristive reconstruction mechanism to realize a tunable penetration depth SPR biosensor under the incident excitation of infrared light.

The present invention has beneficially effects as follows.

The SPR biosensor provided by the present invention adopts the infrared memristor reconstruction electrochemical metallization mechanism, and is able to realize the tenability of the penetration depth of the SPR biosensor.

When there is no bias voltage is applied to the memristive unit, the biosensor forms an LRSPR effect in a highly symmetrical environment, and the penetration depth is able to reach 2.5 μm or more; when the memristive unit is applied with a forward bias voltage, the metal material of the metal film layer of the memristive unit grow metal nanofilaments in the second non-conductive dielectric film layer by redox reaction, the originally symmetrical environment of the dielectric constant of the dielectric layer due to the metal nanofilaments is destroyed, so that the penetration depth of the LRSPR is gradually reduced, and the penetration depth of the sensor is able to be reduced to 1.0 to 1.5 μm, when the memristive unit is applied with a negative bias voltage, the metal nanofilaments grown in the second non-conductive dielectric film layer migrate back to the metal film layer under the action of the reverse electric field, the whole biosensor structure changes back to the case of no voltage bias, which again forms the LRSPR effect in a highly symmetrical environment to restore its ultra-long penetration depth.

Therefore, compared with the prior art, the penetration depth generated by the sensing unit of the biosensor provided by the present invention is able to be dynamically changed in the case where the memristive unit is applied with a positive or negative bias voltage, thereby achieving flexible penetration depth to significantly improve the resolution of unknown material organisms.

BRIEF DESCRIPTION OF THE DRAWINGS

In order to more clearly illustrate technical solutions of embodiments of the present invention, the drawings used in the embodiments will be briefly described as below. It should be understood that the following drawings show only certain embodiments of the present invention and are therefore not considered as limiting the protective scope of the present invention. For those skilled in the art, other relevant drawings can also be obtained according to these drawings without any creative work.

FIG. 4($b$) is a resonance angle map of normalized reflection spectrum when a positive bias voltage is applied to the memristive unit.

FIG. 5($b$) and FIG. 5($c$) are two simulation result graphs of the biosensor when different positive bias voltages are applied to the memristive unit, respectively.

Figure 1:
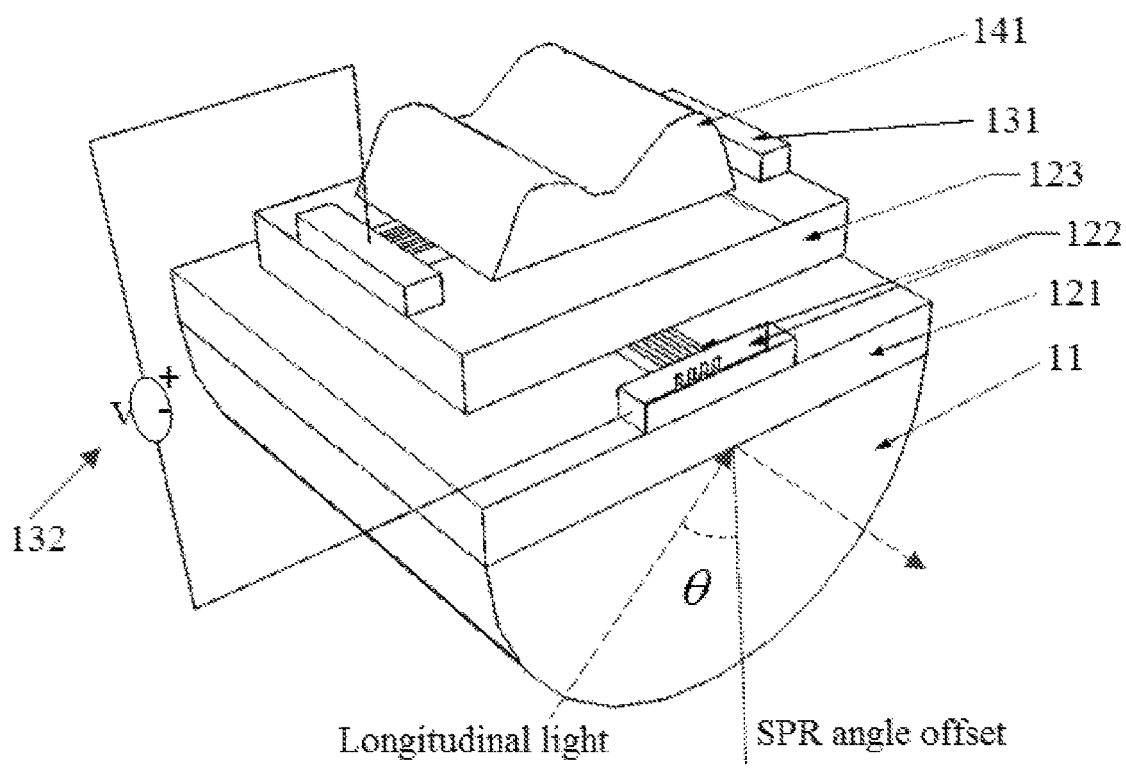
FIG. 1 is a three-dimensionally structurally schematic view of a SPR biosensor according to a preferred embodiment of the present invention.

In the drawings, 11: prism; 121: first non-conductive dielectric film layer; 122: metal film layer; 123: second non-conductive dielectric film layer; 13: memristive unit; 131: conductive dielectric film layer; 132: voltage applying device; 141: biological organism to be tested; θ: incident angle of infrared light.

DETAILED DESCRIPTION OF THE PREFERRED EMBODIMENT

In order to better illustrate the content of the present invention, the present invention is further verified by the preferred embodiments as follows. It should be understood that the embodiments are merely illustrative of the present invention, which are only a part of the present invention and are not intended to limit the present invention.

Figure 2:
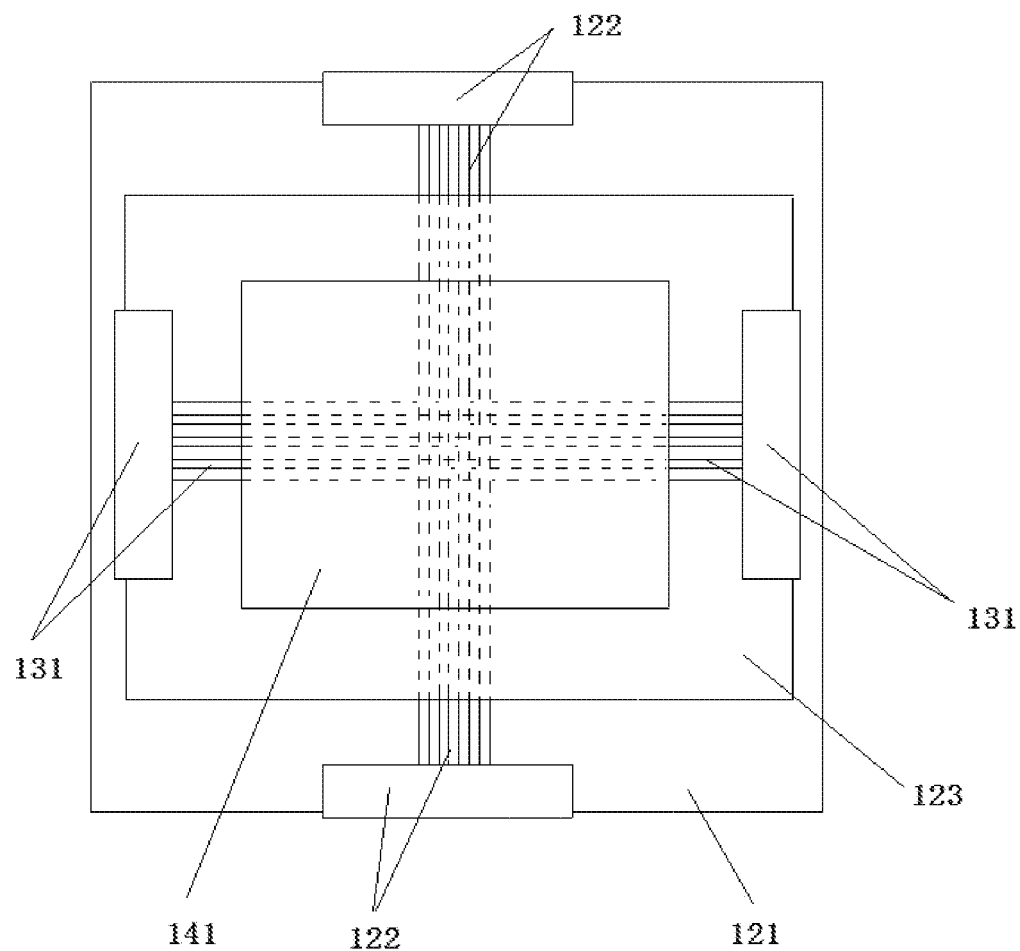
FIG. 2 is a top view of the SPR biosensor according to the preferred embodiment of the present invention, wherein a CROSSBAR structure is expressed by dotted line.
Figure 3:
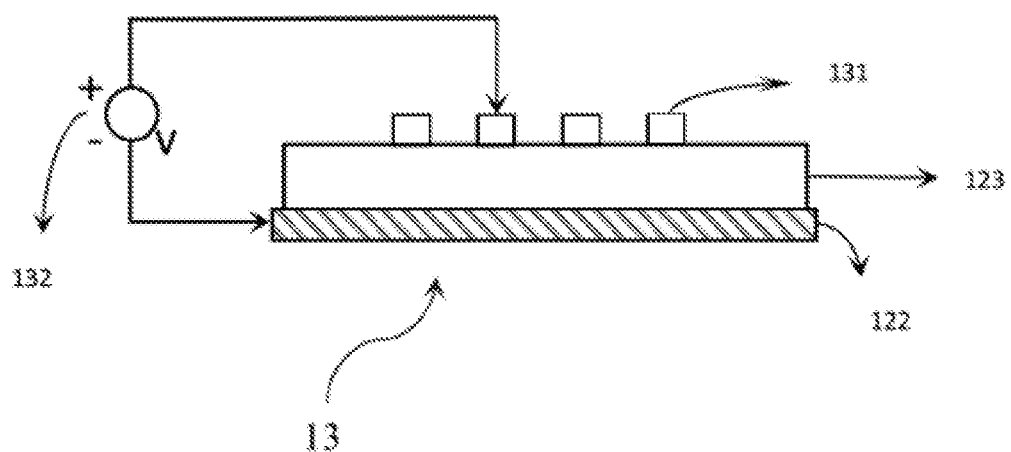
FIG. 3 shows a connection relationship between a memristive unit and a voltage applying device according to the preferred embodiment of the present invention.

Referring to FIGS. 1 and 2 of the drawings, a memristor-reconstructed near-infrared SPR (Surface Plasmon Resonance) biosensor with adjustable penetration depth according to a preferred embodiment of the present invention is illustrated, which comprises:

a prism 11, and a first non-conductive dielectric film layer 121, a metal film layer 122, a second non-conductive dielectric film layer 123 and a conductive dielectric film layer 131 all of which are located at a bottom of the prism 11 in sequence, wherein:

the prism 11 is configured to generate an AIR (Attenuated Total Reflection) attenuation evanescent wave under incident excitation of infrared light;

the first non-conductive dielectric film layer 121, the metal film layer 122, and the second non-conductive dielectric film layer 123 define a sensing unit, the first non-conductive dielectric film layer 121 and the second non-conductive dielectric film layer 123 form a highly symmetric environment, the sensing unit is configured to implement an LRSPR (Long Range Surface Plasmon Resonance) effect so as to realize a basic sensing function of the SPR (Surface Plasmon Resonance) sensor;

the metal film layer 122, the second non-conductive dielectric film layer 123 and the conductive dielectric film layer 131 define a memristive unit 13, wherein: the metal film layer 122 acts as a first electrode, the conductive dielectric film layer 131 acts as a second electrode, the first electrode is perpendicular to the second electrode for forming a CROSSBAR structure, the first electrode is electrically connected with the second electrode, a voltage applying device 132 is provided between the first electrode and the second electrode for applying a positive or negative bias voltage to the memristive unit 13 so as to realize infrared memristive reconfiguration.

Preferably, the prism 11 comprises a prism with a larger refractive index; according to the preferred embodiment, the prism is embodied as a semi-cylindrical Si prism which is configured to generate the ATR (Attenuated Total Reflection) attenuation evanescent wave under incident excitation of infrared light. Of course, the prism is also embodied as a Ge prism. The infrared light has a wavelength of 1310 nm, which is able to balance the low dispersion of the communication wavelength with its own long propagation distance.

According to the preferred embodiment of the present invention, the first non-conductive dielectric film layer 121 is made from a-Si (amorphous silicon) and has a thickness of 200 nm.

According to the preferred embodiment of the present invention, the metal film layer 122 is made of Ag and has a thickness in a range of 35 to 42 nm, and preferably, of 35 nm.

According to the preferred embodiment of the present invention, the second non-conductive dielectric film layer 123 is made from a-Si and has a thickness in a range of 230 to 300 nm, and preferably, of 300 nm.

According to the preferred embodiment of the present invention, the conductive dielectric film layer 131 is made from IMO (indium tin oxide doped with molybdenum), has a refractive index of 1.84 and a thickness in a range of 40 to 60 nm, and preferably, of 50 nm.

In order to ensure that an ohmic contact resistance is small enough, according to the preferred embodiment of the present invention, the first electrode (which is made of Ag) and the second electrode (which is made from IMO) are designed to be perpendicular to each other for forming the CROSSBAR structure, both of the first electrode and the second electrode have a comb-shaped structure which comprises multiple comb teeth, a line width of every comb tooth is 20 nm, and a spacing of every two adjacent comb teeth is 20 nm, a width of each of the first electrode and the second electrode is in a range of 0.2 to 1 µm, a size of each of the first electrode and second electrode is 1×0.5×0.5 µm.

In the FIGS. 1 and 2, a reference sign 141 refers to a biological organism to be tested.

The above-mentioned biosensor is prepared by a method which comprises steps of:

(S1) depositing an a-Si film layer 121 with a thickness of 200 nm on a bottom of a semi-cylindrical Si prism 11 through RF (radio frequency) magnetron sputtering;

(S2) depositing a Ag film layer 122 with a thickness of 35 nm on the a-Si film layer 121 through DC (direct current) magnetron sputtering, performing coating and photoetching on the Ag film layer 122, obtaining multiple first grooves with an equal line width and an equal spacing of 20 nm to form a first electrode of a memristive unit 13 for generating SPR in a sensing unit through light excitation;

(S3) depositing another a-Si film layer 123 with a thickness of 300 nm on the Ag film layer 122 through RF magnetron sputtering;

(S4) depositing an IMO film layer with a thickness of 50 nm on the a-Si film layer 123 in the (S3) through RF magnetron sputtering, performing coating and photoetching on the IMO film layer, obtaining multiple second grooves with an equal line width and an equal spacing of 20 nm to form a second electrode of the memristive unit 13 which combines with the first electrode to form a CROSSBAR structure; and (S5) electrically connecting the first electrode with the second electrode, providing a voltage applying device 132 between the first electrode and the second electrode for applying a bias voltage to the memristive unit 13.

A working principle of the biosensor according to the preferred embodiment of the present invention is as follows.

(1) Implementation of Basic Sensing Function of SPR Biosensor

Figure 4A:
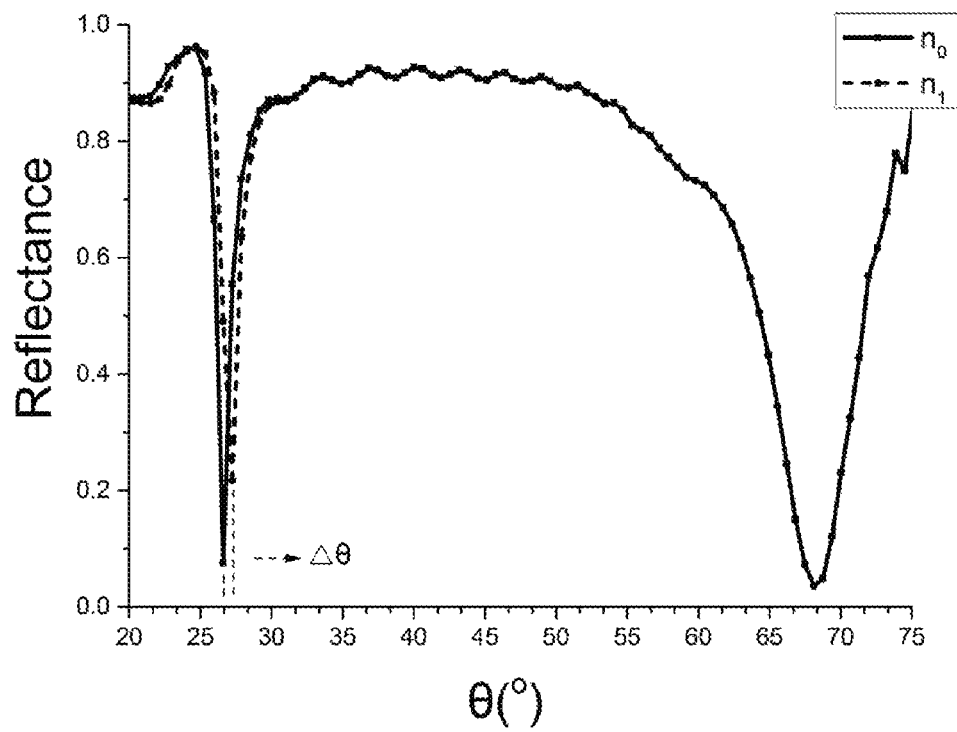
FIG. 4($a$) is a resonance angle map of normalized reflection spectrum when there is no bias voltage is applied to the memristive unit.

When there is no bias voltage is applied to the memrist unit 13, the biosensor according to the preferred embodiment of the present invention comprises the Si prism 11, the a-Si film layer 121 with the thickness of 200 nm, the Ag film layer 122 with the thickness of 35 nm, the a-Si film layer 123 with the thickness of 300 nm, the IMO film layer 131 with the thickness of 50 nm and the biological organism to be tested 141 in sequence. The SPR biosensor adopts an angle mode to align infrared light with a center of the CROSSBAR channel. FIG. 4(a) is a schematic view of a normalized reflection spectrum resonance angle, wherein: when a reflectance of the biological organism to be tested changes from n0 to n1, a resonance angle changes, and a change of the resonance angle is denoted as Δθ, so as to achieve the basic sensing function of the SPR biosensor.

Figure 4B:
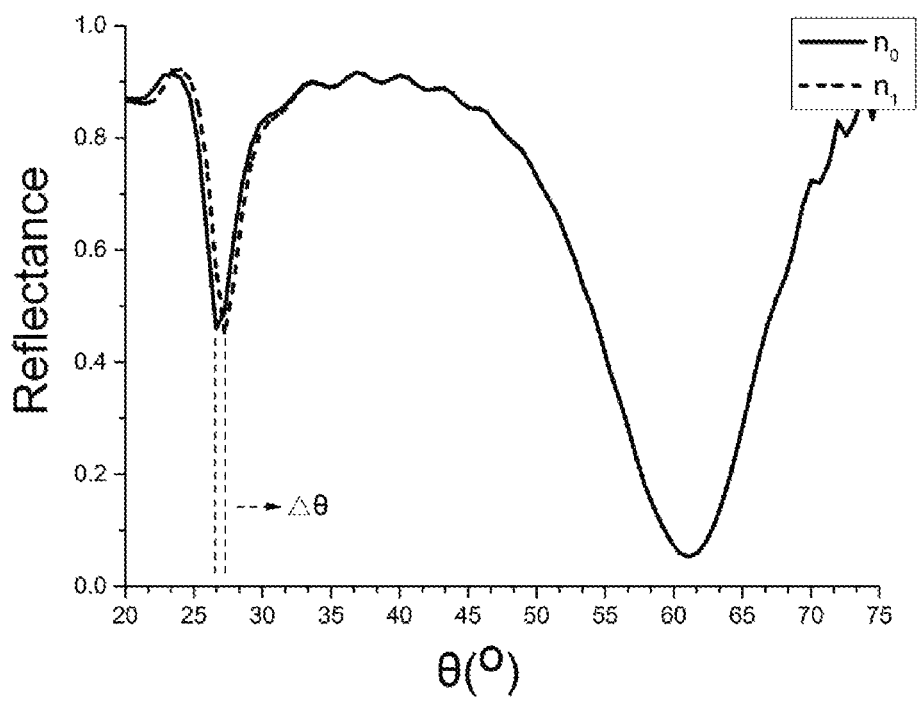

When a positive bias voltage is applied to the memrist unit 13 which has a sandwich structure defined by the Ag film layer 122, the a-Si film layer 123 and the IMO film layer 131, the Ag film layer 122 is electrochemically metallized, and at this time, the biosensor comprises the Si prism 11, the a-Si film layer 121 with the thickness of 200 nm, the Ag film layer 122 with the thickness of 35 nm, the a-Si film layer 123 with the thickness of 300 nm, the IMO film layer 131 with the thickness of 50 nm and the biological organism to be tested 141 in sequence. The SPR biosensor still adopts the angle mode to align infrared light with the center of the CROSSBAR channel. FIG. 4(b) is another schematic view of the normalized reflection spectrum resonance angle, wherein: when the reflectance of the biological organism to be tested changes from n0 to n1, a resonance angle changes, and the change of the resonance angle is denoted as Δθ, so as to achieve the basic sensing function of the SPR biosensor.

(2) Implementation of Penetration Depth Tuning Function

Figure 5A:
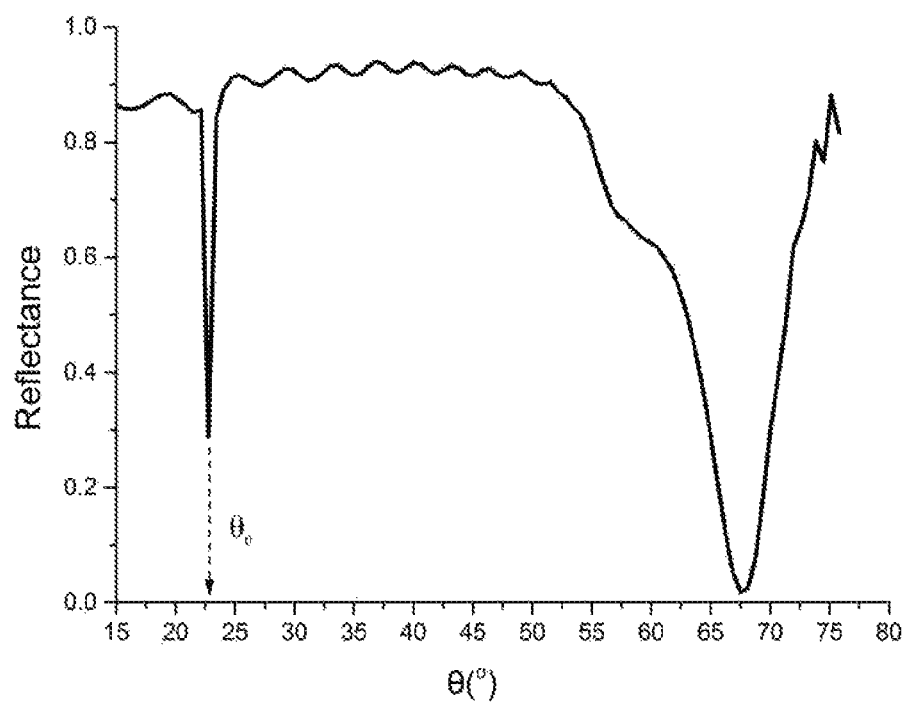
FIG. 5($a$) is a simulation result graph of the biosensor when there is no bias voltage is applied to the memristive unit.

When there is no bias voltage is applied to the memrist unit 3, the SPR biosensor adopts the angle mode to align infrared light with the center of the CROSSBAR channel. FIG. 5(a) is a schematic view of a resonance angle, wherein: the prism is excited by infrared light, and a sandwich structure of the sensing unit defined by the a-Si film layer 121, the Ag film layer 122, and the a-Si film layer 123 forms the LRSRP effect, and at this time, the LRSRP has an ultra-long penetration depth due to its very high symmetrical environment.

Figure 5B:
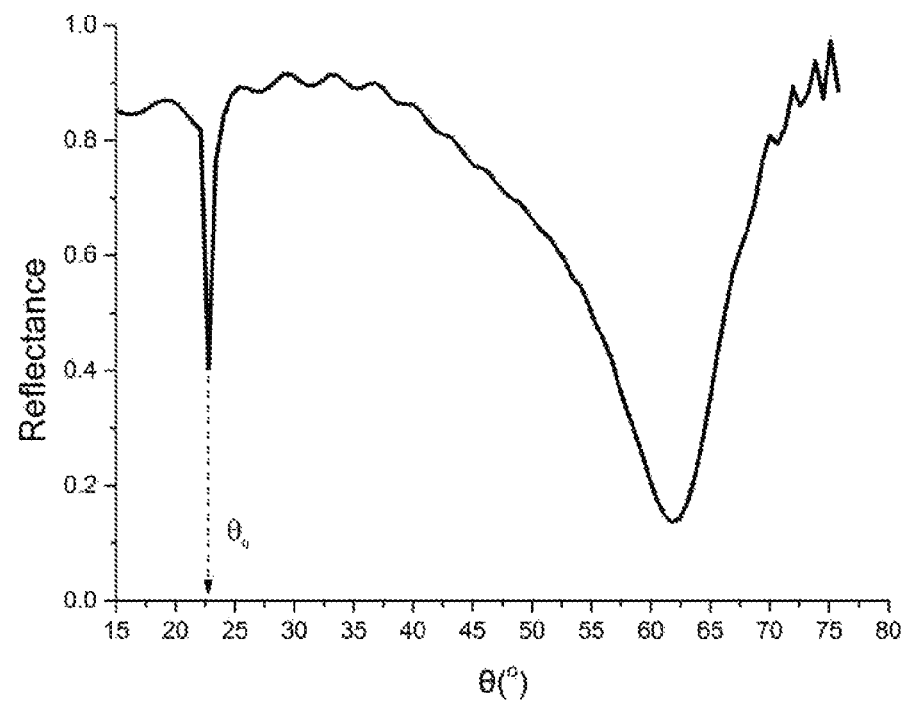
Figure 5C:
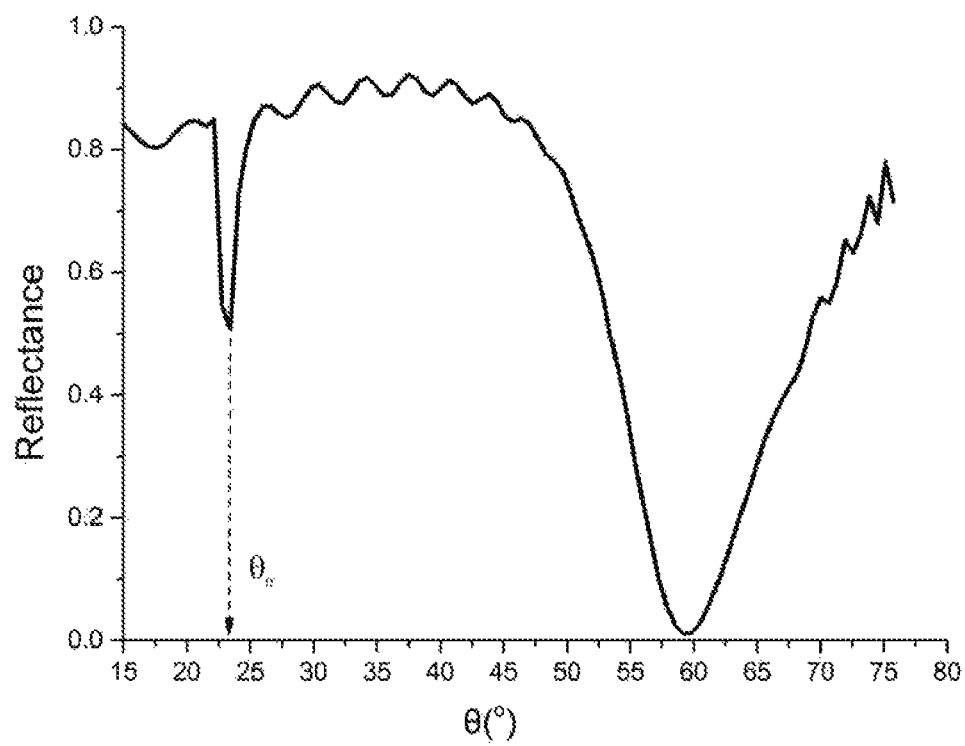

When a positive bias voltage is applied to the memrist unit 13, the SPR biosensor still adopts the angle mode. FIG. 5(b) or 5(c) shows the resonance angle under the excitation of infrared light. When the positive bias voltage is applied to the memrist unit which has the sandwich structure defined by the Ag film layer 122, the a-Si film layer 123 and the IMO film layer 131, the Ag film layer 122 is electrochemically metallized, Ag of the Ag film layer 122 grows metal nanofilaments in the a-Si film layer 123 by redox reaction, and at this time, the biosensor comprises the Si prism 11, the a-Si film layer 121 with the thickness of 200 nm, the Ag film layer 122 with the thickness of 35 nm, the a-Si film layer 123 containing metal nanofilaments, the IMO film layer 131 and the biological organism to be tested 141 in sequence. Due to the reconstitution mechanism of the memristive effect, compared with the original second non-conductive dielectric film layer only containing a-Si, the second non-conductive dielectric film layer containing a-Si and the metal nanofilaments changes in a dielectric constant, which destroys the symmetrical environment of the refractive index of the original device, that is, destroys the formation conditions of LRSPR, so that the penetration depth of the original LRSPR with the ultra-long penetration depth is gradually reduced. Within a positive bias voltage range of 0 v to 10 v, the penetration depth gradually decreases with the bias voltage increases.

Figure 6:
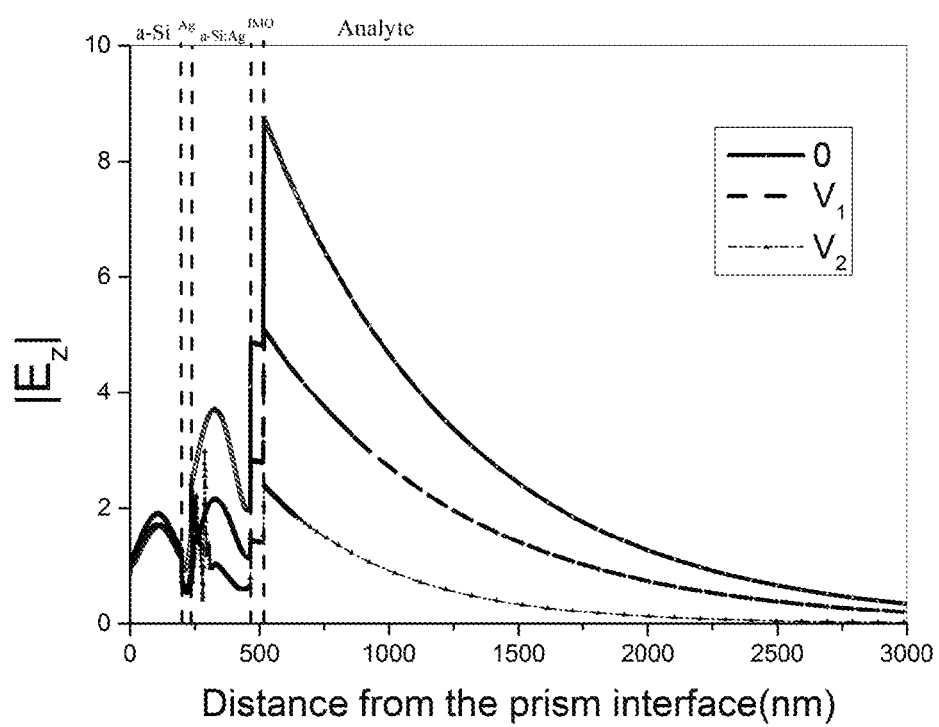
FIG. 6 shows a simulated penetration depth result of LRSPR, wherein "0" denotes that there is no bias voltage is applied to the memristive unit which is corresponding to FIG. 5($a$); "$V_1$" and "$V_2$" respectively denote two simulated penetration depth results of LRSPR when different positive bias voltages are applied to the memristive unit which are corresponding to FIG. 5($b$) and FIG. 5($c$), respectively.

When a negative bias voltage is applied to the memrist unit 13 which has the sandwich structure defined by the Ag film layer 122, the a-Si film layer 123 and the IMO film layer 131, and infrared light is aligned with the center of the CROSSBAR channel, the Ag film layer 122 is electrochemically metallized. In this case, the metal nanofilaments in the a-Si film layer 123 migrate back to the Ag electrode under the action of the reverse electric field, and the structure of the entire biosensor gradually changes back to the no-voltage bias under the incident excitation of infrared light, and at this time, the LRSPR effect is again formed again, the characteristic of ultra-long penetration depth is recovered. Within a negative bias voltage range of −10 v to 0 v, the penetration depth gradually increases with the negative bias voltage increases. FIGS. 5(a), 5(b) and 5(c) show simulation results of the biosensor according to the preferred embodiment of the present invention through an FDTD (finite difference time domain) method. FIG. 6 shows to that the SPR biosensor adopts the angle mode.

When there is no bias voltage applied to the memrist unit 13, the entire biosensor forms the LRSPR effect under highly symmetrical environment. In FIG. 5(a), the normalized reflection spectrum appears double resonance peaks. The penetration depth of the LRSPR is simulated, which is expressed by solid line "0" in FIG. 6, and is able to reach above 2.5 μm.

When a positive bias voltage is applied to the memrist unit, its normalized reflection spectrum is shown in FIGS. 5(b) and 5(c). At this time, since the symmetrical environment of the dielectric constant of the original dielectric film layer is destroyed due to the metal nanofilaments, the penetration depth of LRSPR with the original ultra-long penetration depth is gradually reduced, and the penetration depths corresponding to the broken lines "$V_1$" and "$V_2$" shown in FIG. 6 are about 1.5 μm and 1.0 μm, respectively;

when a negative bias voltage is applied to the memrist unit, the metal nanofilaments grown in the dielectric film layer migrate back to the metal film layer under the action of the reverse electric field, the entire biosensor changes back to the case of no voltage bias, and at this time, the formed LRSPR at highly symmetric environment has the characteristic of ultra-long penetration depth again.

Compared with the prior art, the penetration depth generated by the sensing unit of the biosensor according to the preferred embodiment of the present invention is able to be dynamically changed in the case of applying a positive or negative bias voltage to the memristive unit, so as to achieve flexible penetration depth changes, thereby significantly improving a resolution when detecting unknown material organisms.

The above is a specific embodiment of the present invention, but it is not intended to limit the present invention. Therefore, it should be noted that any modifications and improvements made based on the present invention are intended to fall within the protective scope of the present invention.

What is claimed is:

1. A memristor-reconstructed near-infrared SPR (Surface Plasmon Resonance) biosensor with adjustable penetration depth, which comprises:

a prism, and a first non-conductive dielectric film layer, a metal film layer, a second non-conductive dielectric film layer and a conductive dielectric film layer all of which are located at a bottom of the prism in sequence, wherein:

the prism is configured to generate an ATR (Attenuated Total Reflection) attenuation evanescent wave under incident excitation of infrared light;

the first non-conductive dielectric film layer, the metal film layer, and the second non-conductive dielectric film layer define a sensing unit, the first non-conductive dielectric film layer and the second non-conductive dielectric film layer form a symmetric environment, the sensing unit is configured to implement an LRSPR (Long Range Surface Plasmon Resonance) effect so as to realize a basic sensing function of the SPR (Surface Plasmon Resonance) sensor;

the metal film layer, the second non-conductive dielectric film layer and the conductive dielectric film layer define a memristive unit, wherein: the metal film layer acts as a first electrode, the conductive dielectric film layer acts as a second electrode, the first electrode is perpendicular to the second electrode for forming a CROSSBAR structure, the first electrode is electrically connected with the second electrode, a voltage applying device is provided between the first electrode and the second electrode for applying a positive or negative bias voltage to the memristive unit so as to realize infrared memristive reconfiguration.

2. The memristor-reconstructed near-infrared SPR biosensor with adjustable penetration depth, as recited in claim 1, wherein: the prism is a Si or Ge prism with a larger refractive index which is able to satisfy conditions of total reflection of light waves.

3. The memristor-reconstructed near-infrared SPR biosensor with adjustable penetration depth, as recited in claim 2, wherein: the first non-conductive dielectric film layer is made from a-Si and has a thickness in a range of 180 to 220 nm.

4. The memristor-reconstructed near-infrared SPR biosensor with adjustable penetration depth, as recited in claim 2, wherein: the metal film layer is made of Ag and has a thickness in a range of 35 to 42 nm.

5. The memristor-reconstructed near-infrared SPR biosensor with adjustable penetration depth, as recited in claim 2, wherein: the second non-conductive dielectric film layer is made from a-Si and has a thickness in a range of 230 to 300 nm.

6. The memristor-reconstructed near-infrared SPR biosensor with adjustable penetration depth, as recited in claim 2, wherein: the conductive dielectric film layer is made from IMO (indium tin oxide doped with molybdenum), and has a thickness in a range of 40 to 60 nm.

7. The memristor-reconstructed near-infrared SPR biosensor with adjustable penetration depth, as recited in claim 1, wherein: the first non-conductive dielectric film layer is made from a-Si (amorphous silicon) and has a thickness in a range of 180 to 220 nm.

8. The memristor-reconstructed near-infrared SPR biosensor with adjustable penetration depth, as recited in claim 1, wherein: the metal film layer is made of Ag and has a thickness in a range of 35 to 42 nm.

9. The memristor-reconstructed near-infrared SPR biosensor with adjustable penetration depth, as recited in claim 1, wherein: the second non-conductive dielectric film layer is made from a-Si and has a thickness in a range of 230 to 300 nm.

10. The memristor-reconstructed near-infrared SPR biosensor with adjustable penetration depth, as recited in claim 1, wherein: the conductive dielectric film layer is made from IMO (indium tin oxide doped with molybdenum), and has a thickness in a range of 40 to 60 nm.

11. The memristor-reconstructed near-infrared SPR biosensor with adjustable penetration depth, as recited in claim 1, wherein: both of the first electrode and the second electrode have a comb-shaped structure which comprises multiple comb teeth, a line width of every comb tooth is 20 nm, a spacing of every two adjacent comb teeth is 20 nm, a width of each of the first electrode and the second electrode is in a range of 0.2 to 1 µm, and a size of each of the first electrode and second electrode is 1×0.5×0.5 µm.

12. A method for tuning a penetration depth of the memristor-reconstructed near-infrared SPR biosensor with adjustable penetration depth of claim 1, which comprises steps of:
   applying a positive bias voltage to the memristive unit by a voltage applying device, electrochemically metallizing the metal film layer, a metal material of the metal film layer growing metal nanofilaments in the second non-conductive dielectric film layer through oxidation-reduction, changing a dielectric constant of a partial area of the original second non-conductive dielectric film layer, destroying a symmetrical environment of the first non-conductive dielectric film layer and the second non-conductive dielectric film layer of the sensing unit, and reducing the penetration depth of the sensor; or
   applying a negative bias voltage to the memristive unit by the voltage applying device, migrating the metal nanofilaments in the second non-conductive dielectric film layer back to the metal film layer; restoring the symmetrical environment of the first non-conductive dielectric film layer and the second non-conductive dielectric film layer of the sensing unit, and reducing the penetration depth of the sensor; and restoring the penetration depth of the sensor back to a penetration depth without applying the negative bias voltage to the memristive unit.

13. A method for manufacturing a memristor-reconstructed near-infrared SPR biosensor with biosensor with adjustable penetration depth, which comprises steps of:
   (S1) depositing a first non-conductive dielectric film layer on a bottom of a prism through RF (radio frequency) magnetron sputtering;
   (S2) depositing a metal film layer on the first non-conductive dielectric film layer through DC (direct current) magnetron sputtering, performing coating and photoetching on the metal film layer, obtaining multiple first grooves with an equal line width and an equal spacing to form a first electrode of a memristive unit for generating SPR (Surface Plasmon Resonance) in a sensing unit through light excitation, wherein the equal line width is as same as the equal spacing;
   (S3) depositing a second non-conductive dielectric film layer on the metal film layer through RF magnetron sputtering;
   (S4) depositing a conductive dielectric film layer on the second non-conductive dielectric film layer through RF magnetron sputtering, performing coating and photoetching on the conductive dielectric film layer, obtaining multiple second grooves with the equal line width and the equal spacing to form a second electrode of the memristive unit which combines with the first electrode to form a CROSSBAR structure; and
   (S5) electrically connecting the first electrode with the second electrode, providing a voltage applying device between the first electrode and the second electrode for applying a bias voltage to the memristive unit.

* * * * *